United States Patent [19]
Mott

[11] Patent Number: 6,080,125
[45] Date of Patent: Jun. 27, 2000

[54] ABDOMINAL POSTOPERATIVE BINDER

[76] Inventor: George E. Mott, 10619 Tower Oaks, Houston, Tex. 77070

[21] Appl. No.: 08/856,813

[22] Filed: May 15, 1997

[51] Int. Cl.[7] .............................. A61F 13/00; A61F 5/24; A61F 5/28; A41B 9/00
[52] U.S. Cl. ................................ 602/61; 602/60; 602/61; 602/67; 602/75; 128/96.1; 128/99.1; 128/100.1; 450/140; 2/401
[58] Field of Search ................................ 450/94, 95, 155, 450/117, 107, 122, 140; 2/464, 466, 78.1, 78.2, 109, 400, 408, 78.3, 401, 402, 406, 407, 465, 311, 312; 602/60, 63, 67, 68, 69, 70, 73, 79, 19, 61, 64, 74, 75, 76, 77; 604/385.1, 385.2; 128/99.1, 100.1, 101.1, 102.1, 96.1

[56] References Cited

U.S. PATENT DOCUMENTS

| | | | |
|---|---|---|---|
| 79,994 | 7/1868 | Lindley | 128/100.1 |
| 156,050 | 10/1874 | Washburn | 128/100.1 |
| 647,551 | 4/1900 | Bain | 128/100.1 |
| 2,355,740 | 8/1944 | McNees | 604/407 |
| 2,605,762 | 8/1952 | Balisterieri | 128/96.1 |
| 2,684,673 | 7/1954 | Lerman | 2/403 |
| 3,393,674 | 7/1968 | Nelkin | 128/96.1 |
| 3,895,629 | 7/1975 | Snyder | 604/19 |
| 4,059,103 | 11/1977 | Glaser | 128/96.1 |
| 4,446,575 | 5/1984 | Davis | 2/400 |
| 4,932,079 | 6/1990 | Bridgewater | 2/313 |
| 5,003,972 | 4/1991 | Kestler | 602/70 |

*Primary Examiner*—Kim M. Lee
*Attorney, Agent, or Firm*—Arthur M. Dula

[57] ABSTRACT

The invention is a postoperative binder made of relatively inelastic material that is cut to fit the patient and held in place by Velcro® binders. The present invention uses mechanical, rather than elastic, compression. Mechanical loads are carried near or on the hip joint, either by physically hooking the binder over the hips or attaching it to an elastic band that rides on or above the patient's hips. The present invention provides mechanical support to lower abdominal tissue, especially near the genitals and in the area of the peritoneum.

3 Claims, 2 Drawing Sheets

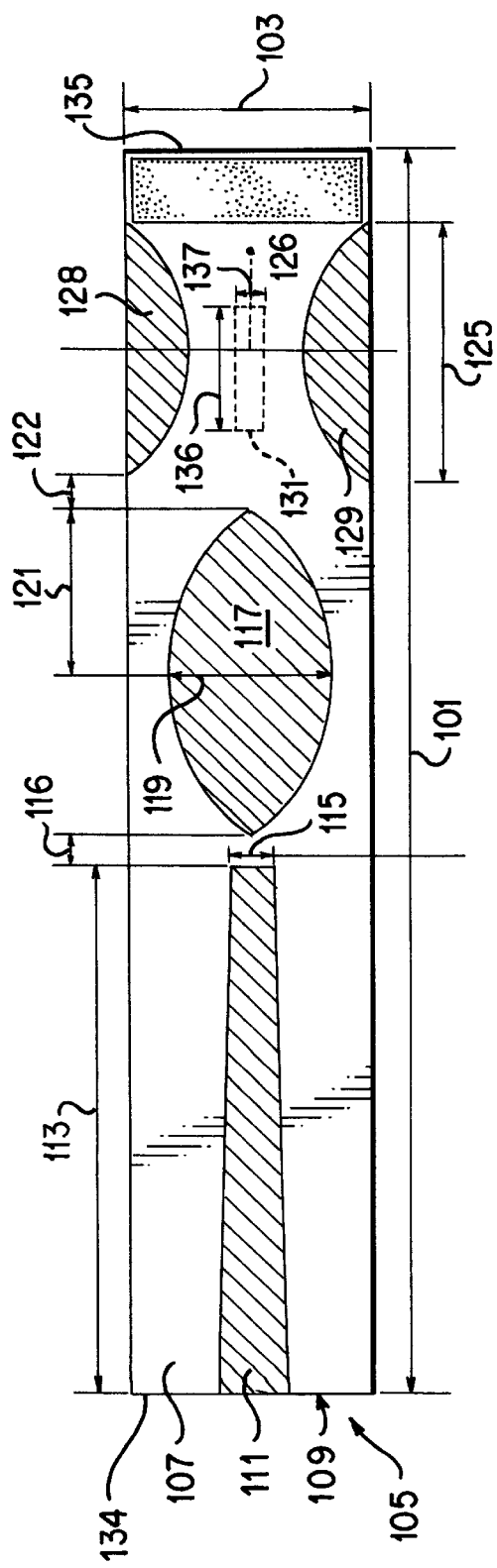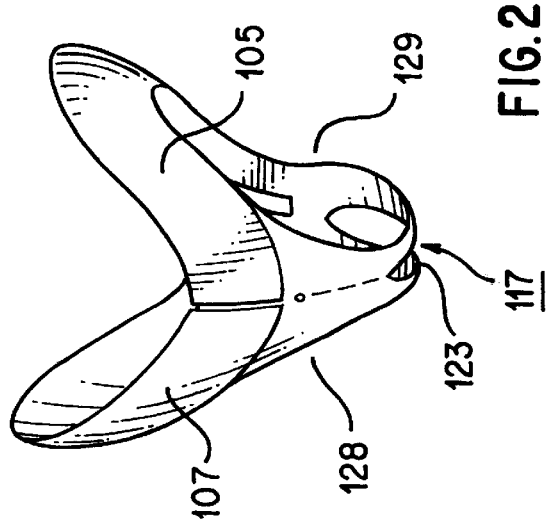

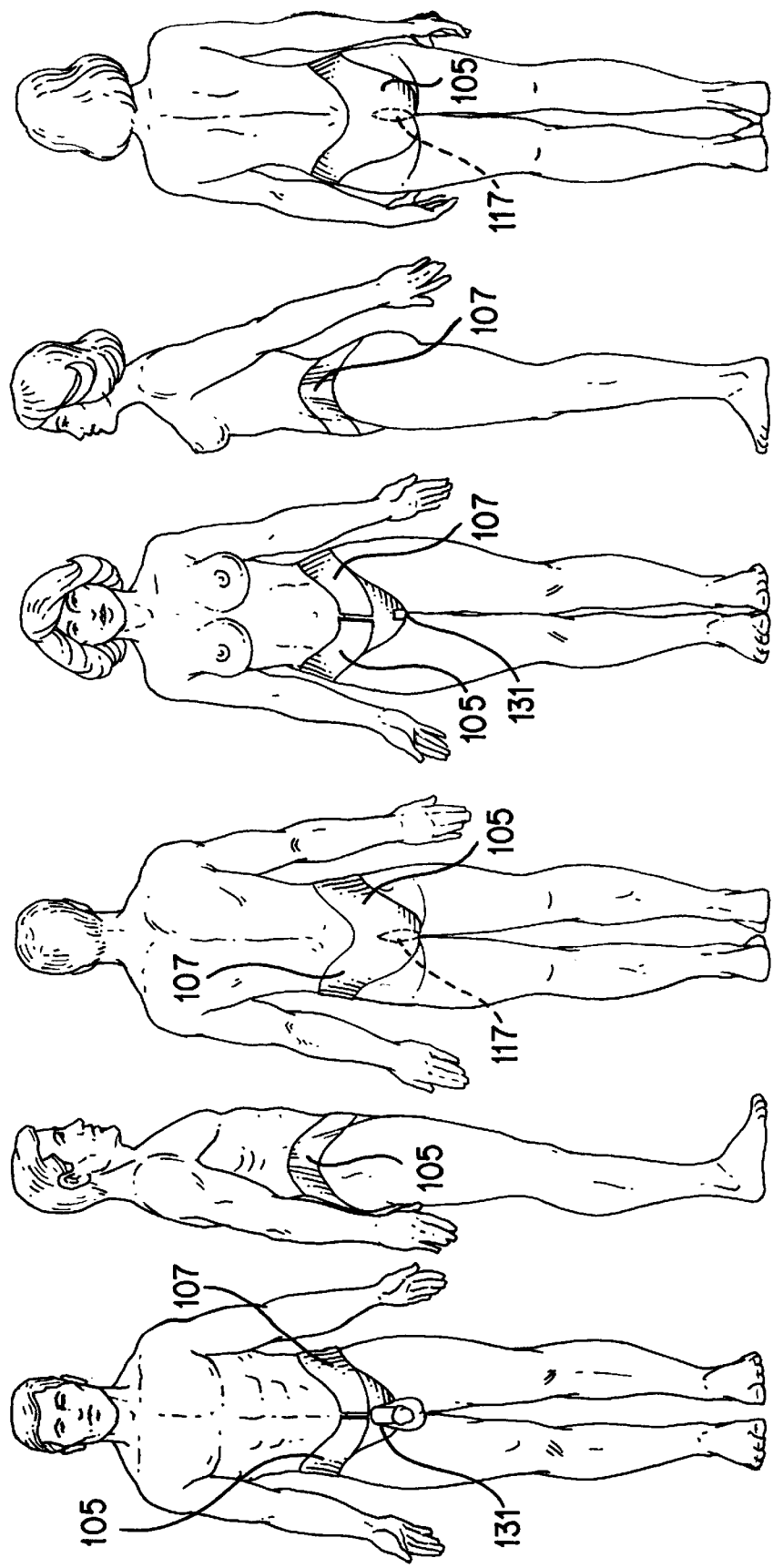

ABDOMINAL POSTOPERATIVE BINDER

BACKGROUND OF THE INVENTION

1. Field of the Invention

The invention is an improvement in medical support garments. More specifically the present invention is a postoperative support binder for patient use after abdominal surgery to control pain, edema and infection, whereby postoperative complications are reduced and recovery time and postoperative mobility of patients is improved.

2. Background of the Prior Art

Patients who have undergone aesthetic or reconstructive surgery of the abdomen, genitals or pelvis are likely candidates for some form of complications during the recovery period. Typical complications are atelectasis, hypostatic pneumonia, phlebitis and pulmonary complications. Clinical evidence indicates that 20 to 40 percent of patients will experience pulmonary complications (Bartlett, Robert H. et al., *Respiratory Maneuvers to Prevent Post-Operative Pulmonary Complications*, JAMA, Vol. 224, No. 7,(1973). Thus it is important that the rehabilitation program encourage and develop the return of respiratory efficiency.

Early ambulation is a key factor in helping the patient reestablish his normal physiology and preventing or minimizing postoperative complications. Ambulation hastens muscle redevelopment, wound healing (Brunner, Lillian Sholtis, et al., *The Textbook of Medical Surgical Nursing* (Second Edition, Lippincott, Philadelphia, 1978) p. 134.) and the return of vital lung capacity (Ali, J. and Khan, T. A., *The Comparative Effects of Muscle Transection and Median Upper Abdominal Incision on Post Operative Pulmonary Function, Surgery, Gynecology & Obstetrics*, Vol. 148, No. 6, (1979)).

The prior art teaches the use of binders or girdles that use the elastic properties of fiber to provide abdominal support, such as U.S. Pat. No. 5,571,039, issued to Ford in 1994. This abdominal support comprises a plurality of webs having therein elastic fibers, said web forming the girdle that fits around at least a portion of the abdomen, hips and buttocks of the patient. Another example is the waist support and hip girdle taught by U.S. Pat. No. 3,783,879 issued to Stalder in 1971, which teaches use of a knitted elastic fabric with an open mesh.

The best prior art known to the present inventor is the commercial postoperative binders sold by the Veronique Compression Wear company of San Leandro, Calif.; and the Dale® Abdominal Binder, sold by Dale Medical. All of the prior art known to the inventor depends primarily on the elastic properties of the material forming the binder to provide the compression. The use of such postoperative compression clothing is a well-established medical practice. Abdominal binders have been assigned Medicare/Medicaid reimbursement codes L0960 or A4465.

The prior art has a problem. The prior art uses the stretch of an elastic fiber to provide compression, the garments tend to roll, 'rope' or bunch up. Also elastic force is insufficient to control edema. They provide the least pressure where there is swelling, as elastic conforms to the body shape of the patient.

BRIEF DESCRIPTION OF THE INVENTION

The present invention is a postoperative binder made of relatively inelastic material that is cut to fit the patient and held in place by Velcro®. The present invention uses mechanical, rather than elastic, compression in this relatively inelastic material. Mechanical loads are carried near or on the hip joint, either by physically hooking the binder over the hips or attaching it to an elastic band that rides on or above the patient's hips. The present invention provides greater mechanical support to lower abdominal tissue, especially near genitals and in the area of the peritoneum, than is possible using prior art elastic binders. This solves the problem of fluid tissue water retention and long healing times that are not answered by existing designs.

The invention's special industrial utility comprises:
a. Obesity surgery: male or female
b. Postoperative wound care: especially for diabetic, immune compromised (AIDS) or vascular insufficiency.
c. Military wounds/trauma: especially crushing injury, blast injury, gun shot, blunt trauma (car wreck), military field stabilization to control bleeding in lower abdomen and/or upper portion of lower extremities.
d. Penile surgery: penile augmentation, penile amputation (cancer); penile reconstruction.
e. Vaginal delivery, caesarian section wounds.
f. General surgery: hernia repair, abdominal and/or rectal cancer resection, orthopedic surgery, total hip replacement (support for rotary abductor box); hip nailing.
g. Hyperbaric care: scrotal lymph edema, section wounds in obese patients or those who are immune or vascularly compromised; difficult wound healing.
h. Sex change surgery For the state of the art please see:
1. Weiss, E. B., Dale Combo Abdominal Binders—A Study in a Post-Operative Setting, (Independent clinical study conducted at St. Vincent's Hospital, Worcester, Mass. Date available on request.)
2. Khan, T. A., Serrette, C., and Ali, J., The Effect of Abdominal Binders on Postoperative Pulmonary Function, Infections in Surgery, Vol. 2., No. 1L pp. 875–881, November 1983.
3. Finn, Kathleen, How's Your Post-Op Ambulation Technique? R.N., Vol. 42, page 9.

Abdominal Surgery in General

After open abdominal surgery, the patient may avoid the very activities that can help restore normal pulmonary function and muscle redevelopment. These activities are deep breathing, coughing, and ambulation. To the patient even the thought of sitting up or getting out of bed may seem forbidding and coughing can be a frightening experience. Under these circumstances, the patient needs instruction and direct physical assistance in splinting coughs, maneuvering in and out of bed, breathing, and walking erect.

Patients with abdominal incisions tend to hunch over in an attempt to splint the wound, and need frequent reminders to straighten up. It may help to explain that good posture promotes healing by exerting just enough tension on abdominal muscles to strengthen them without disrupting the wound. Slouching, on the other hand, throws the patient off balance, discourages deep breathing, and strains back muscles.

Frequently, when a patient wakes up in recovery he inadvertently coughs and immediately discovers how painful the wound is. Thereafter, the patient may intentionally or subconsciously suppress future coughs in order to minimize the painful experience. This is of course counter to the prescribed necessity of initiating deep breathing, coughing and ambulation.

The nurse in the unit may teach the patient how to splint the wound with a pillow to lessen the pain. But often, when the nurse leaves, the patient puts down the pillow and fails to continue his or her instructions. Application of the binder allows the patient to perform required breathing and other activities in a manner that is more comfortable, less painful and without supervision.

The present invention helps to overcome the patient's reluctance to engage in therapeutic activities. The present invention used with Velcro® fasteners is more effective and easier to apply than the many-tailed scultetus binder that fastened with safety pins.

Gall Bladder Surgery

Patients recovering from traditional gall bladder surgery are especially prone to pulmonary complications as are all patients with upper abdominal incisions. It is recommended that these postoperative patients be gotten out of bed as soon as possible to prevent pulmonary complications. The present invention can insure greater comfort while aiding and encouraging coughing and deep breathing.

Bariatric Procedures

In surgical treatments of the morbidly obese such as vertical banded gastroplasty or gastric resection, an abdominal binder has many applications for the patient in the early postoperative period. It lessens the danger of pulmonary complications by encouraging deep breathing and coughing and helps to counteract the patient's natural tendency toward shallow breathing. The present invention makes it easier for the patient to move and turn comfortably. It allows earlier ambulation thus promoting increased respiratory exchange. The abdominal binder, supporting the incision, helps to guard against wound evisceration and infection during the healing process (The Lippincott Manual of Nursing Practice (Lippincott, Philadelphia, 1974) p. 394.) It also helps to control distention and prevent herniation of the peritoneum, as well as unwanted fluid buildup.

Plastic and Cosmetic Surgical Procedures

The use and application of binders to assist postoperative activity for 2 to 4 weeks after abdominal liposuction/lipectomy and/or abdominoplasty is common and well documented. (Newman, Julius, M.D., Bergermeister, Herman, M.D., Golshai, Mohammad, M.D., *Closed Lipo-Sweep Abdominal Liposuction*, The American Journal of Cosmetic Surgery, Vol. 8, No. 1 1991.) Unlike the prior art binders or elastic garments, the present invention is constructed of relatively inelastic material that facilitates patient movement, yet will not "ride up", roll, or rope during use.

The construction of the present invention allows the surgeon to cut holes anywhere on the binder to allow for drainage tubes without the material running or fraying. The present invention can be used to secure the taping that is used to help bind the sections of skin together to prevent splitting of the incision, and promote scarring. (Matarasso, Alan, M.D, Abdominolipoplasty: *A System of Classification and Treatment for Combined Abdominoplasty and Suction-Assisted Lipectomy, Aesthetic Plastic Surgery*, 15111–121 1991.)

Use of the present invention also encourages post-op movement to prevent muscular atrophy and fluid build-up (seroma) which is often associated with abdominoplasty and extensive suction lipectomy.

Hernia Repair

In addition to good general postoperative care, the nurse, in caring for the patient who has had an operation for a hernia, should prevent tension on the newly repaired tissues. If a cough occurs, medications are usually prescribed to depress the cough reflex. They should be given as ordered to prevent paroxysms of coughing and subsequent strain on the repair. (Shaefer, Kathleen Newton, et al., Medical Surgical Nursing (CV Mosby, St. Louis, 1971) p. 615. Use of the present invention can serve to support the incision area, lessen the pain of coughing, and promote the healing process.

Obstetrics and Gynecology

General

In certain post-hysterectomy cases where a tumor has been large enough to cause a marked relaxation of the abdominal wall, wearing an abdominal binder is recommended after surgery. Following an abdominal hysterectomy, the patient may require additional support of the incised abdominal musculature, particularly during ambulation and especially if her abdomen is large or its musculature weak. The present invention can be used to provide the additional support during the healing process. (Nursing Care of the Patient with Medical Surgical Disorders (McGraw-Hill, New York, 1971) p.124.

The post-operative nursing care after cystectomy is similar to that for abdominal surgery, except for one particular. The marked decrease in intra-abdominal pressure incidental to the removal of a large cyst often leads to considerable abdominal distention. This complication may be prevented to some extent by the application of a pad or abdominal binder.

Cesarean Section

After cesarean section, as with other types of open abdominal surgery, the patient will find an increased level of confidence in sitting up, ambulating, and resuming other post-op activities if the binder is used. While the incision of the procedure does not cut through muscle or compromise the diaphragm, the incision is nevertheless long and painful. The present invention will enable the patient to move freely and perform any prescribed incentive breathing program, without the fear of the sutures breaking, or the wound eviscerating.

Post-Partum

Following delivery, a woman may be advised by her physician to use a binder if her abdomen is unusually flabby or pendulous, and, if her musculature has been weakened by the pregnancy (Henderson, Va. and Nite, Gladys, Principles & Practice of Nursing (Sixth Edition, Macmillan, New York 1978) p. 1442.) This is particularly important psychologically if the woman believes she would be more comfortable with some support. The present invention provides added encouragement needed when ambulation is prescribed, and muscle redevelopment will proceed normally to overcome the problem. When the woman is ambulatory, the use of the present inveniton is preferable to a scultetus binder or other prior art compression clothing because it will stay in place and offer overall support as she moves about.

Urological Procedures

For the patient after kidney or bladder surgery, turning, deep breathing, and coughing are extremely important activities to perform in order to minimize the possibility of atelectasis and pneumonia. Such activities are very painful because of the proximity of the incision to the diaphragm. Pain medication, administered with sufficient time for the narcotic effect to take hold, and the application of the present invention will allow the patient to cough and do deep breathing exercises more effectively and efficiently.

BRIEF DESCRIPTION OF THE DRAWINGS

FIG. 1 is a plane view of the form of the present invention, laid flat;

FIG. 2 is an isometric view of the present invention as it is used on a patient;

FIGS. 3*a*, 3*b* and 3*c* show the front, side and back views, respectively, of the present invention on a male patient;

FIGS. 4*a*, 4*b* and 4*c* show the front, side and back views, respectively, of the present invention on a female patient.

DESCRIPTION OF THE PREFERRED EMBODIMENT OF THE INVENTION

In FIG. 1, a generally rectangular sheet of relatively inelastic material, such as commercial Neoprene®, has a length 101 and a width 103 which are chosen to be generally fitting to the majority of patients.

The structure of the binder taught by the present invention is defined by cutting this rectangular sheet to fit the patient, as will be further discussed below.

At a tail end 105 of the sheet a rectangular tapering cutout 111 is made that defines a first leg or tail 105 and a second leg or tail 107. This cut has a tapering width 115 and a length 113, as shown in FIG. 1.

An uncut length 116 of the sheet separates rectangular cut out 111 from a football shaped cut out 117, which has a minor axis 119 and a major semi axis 121. This football shaped cut out section is separated by uncut section 122 from two curve-shaped side cut outs 128 and 129 positioned on left and right ledges of the sheet, respectively, which are opposite one another on the sheet. These cut outs 128 and 129 have a length 125 and is a greatest width 126. Between cut outs 128 and 129 is a rectangular cut out 131, having a length 136 which is greater than its width 137.

A cut-out end 134, opposite the tail end of the sheet is covered with a Velcro® fastener 135, whereby ends of tails 105 and 107 removably attaches to said cut-out end of said sheet by means of Velcro® fasteners.

The size of the sheet which forms the binder taught by the present invention is selected to match the size of the patient to whom it will be fitted and the cut outs defined above are sized by cutting them to fit the shape of the individual patient.

The binder taught by the present invention may be made of any material that is flexible and relatively inelastic.

FIG. 2 shows an isometric view of the binder taught by the present invention. In FIG. 2 the same structures have the same numbers as in FIG. 1, described above. As shown in FIG. 2, cut out 117 defines an anal opening in the binder. Cut outs 128 and 129 define leg openings, together with tails 105 and 107. Ends 134 of the binder is shown under and attached to the ends of tails 105 and 107.

FIGS. 3a, 3b and 3c show the front, side and rear view of the binder taught by the present invention on a male patient. In these figures similar numbers as in FIG. 1 denotes similar structures. These views are presented to show how the invention's tails 105 and 107, each having a length 113, ride over the hips of the patient such that the mechanical load maintained by the binder on the patient are carried by the hip bones. If the patient is obese, the present invention may be affixed to an elastic band, not shown, that rides around the patient's hips. Such band holds the invention on the patient, but its elastic property does not provide compression, which is inelasticly provided mechanically by the invention. This figure also shows how the penis of the male patient protrudes through the opening 131 of the invention. This is important because the penile and anal opening of the invention, as they are individually sized and fitted to each patient, allow the binder taught by the present invention to be worn during the entire post operative period.

FIGS. 4a, 4b and 4c show the present invention on a female patient.

The determination factor in the proper fit of a binder is not a person's size but his lung expansion. Inspiration and expiration vary considerably in individuals of the same stature due to differences in age, health, activity, and the physical capacity of their lungs. Many binders which are sized to fit the "small" medium or "large" person do not address the critical issue of lung expansion and may well be too large or too small. Binders with widely spaced Velcro® fasteners allow closure only at fixed intervals which may not match the patient's need.

The present invention, on the other hand, is totally adjustable, since it is sized and cut to fit the individual patient. Velcro® closures may be placed at any point on the circumference of the binder. Predetermined attachment panels no longer dictate binder closure. Rather, the present invention provides limitless patient fit.

The present invention's use of flexible, but relatively inelastic material provides compression around the entire body resulting in superior, equally distributed support. While offering controlled compression, the present invention allows for sudden lung expansion, as in coughing, and the demands of deep breathing therapy.

The binder closing may be diagonally positioned instead of straight. With diagonal closure, fit may be snugger at top and looser at bottom or vice versa; in this way pressure on the upper and lower abdomen may be varied to suit the patient's particular condition. For example, if the incision is in the lower abdomen it may be desirable to have less pressure on that area, while maintaining maximum pressure on the rest of the abdomen.

For graduated fit with an angled closure, pull the appropriate end of the binder to the desired tautness for the snugger fit, then press-close Velcro at that end on a diagonal. As you continue to press-close from top to bottom or bottom to top, the diagonal angle creates a graduated fit which is loosest at the opposite end from which you began. The greater or lesser the angle at which the closure is begun will determine the degree of graduation from snuggest to loosest.

Applying the Binder

The patient should be supine. The patient is measured and the binder cut to fit. Place the binder smoothly under the patient and, using the patient's weight to hold the binder in place, pull both ends 105 and 107 of the binder outward from the body. Pull the ends together until the necessary compression has been reached. Proper tension is the key to getting optimal binder benefit.

Make sure the binder is wrapped around the lower abdomen, comfortably below the diaphragm so that it doesn't interfere with respiration, and fits securely, but not tightly, over the iliac crest.

Press-fasten the Velcro® closure 135 from the bottom of the binder upward in the direction of venous return, adjusting for the desired compression. Properly placed, low enough on the umbilical area to support abdominal muscles.

Use With Drainage Tubes

The inelastic material of the present invention is designed to accommodate the use of surgical drainage tubes. However, care must be exercised in applying the binder so as not to cause discomfort or irritation to the wound site. Drainage tube occlusion can be prevented by layering surgical sponges on both sides of the drain on the patient's abdomen prior to applying the binder.

If Penrose-type drains are being used, holes should be cut in the binder to accommodate the tubes. Avoid placing the overlapped thickness of the binder over the drainage site. Mark an "X" on the Neoprene® where the hole will be made, crease the material at this point and make an elliptical cut in the material. When the Neoprene® is tensioned, the elliptical cut will become a round hole to accommodate the drain. The diameter of the hole will be equal to the length of the cut. Brush away any loose fibers that have separated from the fabric. The binder will not tear or ravel where a cut has been made.

Care Instructions

In normal hospital use, the present invention requires minimal care. When soiled, it may be machine or hand-washed in a mild detergent. Warm or cold water temperature is recommended. Before washing, make sure surfaces are securely fastened to prevent lint from gathering in the Velcro fibers weakening their locking properties. The binder may be hung dry. Binder sterilization is rarely necessary, but gas sterilization may be used if required. There are no special storage requirements.

The flexible relatively inelastic material used by the present invention can be engaged and disengaged an indefinite number of times. Although some distortion may occur, this condition does not compromise the holding power of the invention.

Home Use

Upon discharge from the hospital, patients may take the binder home for continued benefits both during and after recovery. They will find that the binder fits inconspicuously under clothing to provide comfortable support as they engage in normal activity.

The patient may be instructed that self-application is easy, as follows:

1. Position tails 105 and 107 of the invention over the hips and tension the binder.
2. Wrap around
3. *Press Velcro section 135 closed.*

The binder may also be applied in the same way while lying down.

Clinical Experience

The binder taught by the present invention has been used clinically 110 times with male patients in the following procedures:

1. Phalloplasty augmentation and phialloplasty enhancement (girth)
2. Reconstruction of penile surgery.
3. Scar revisions.
4. Liposuction of pubic area and abdomen.

The recovery time of these patients has improved by six weeks and their rate of infection has decreased by 40 percent as compared with patients undergoing the same surgical procedures who did not use the present invention.

Although the inventor has described a specific embodiment of his invention in this specification and drawings, these are only illustrative of the invention. The scope of the invention should be limited only be the appended claims and their legal equivalents.

What is claimed is:

1. A medical binder for use on a patient, the patient having an iliac crest and an abdomen, comprising:

a generally rectangular sheet of flexible, relatively inelastic material, said sheet having a tail end and a cut-out end, said tail end and said cut-out end being spaced apart by the length of said sheet, said sheet further having a right side curve-shaped cut-out area on a right edge of said sheet proximate said cut-out end of said sheet and a left side curve-shaped cut-out area on a left edge of said sheet spaced apart from said right side curve-shaped cut-out area by a width of said sheet; the shape of said right side curve-shaped cut-out and said left side curve-shaped cut-out being selected such that the binder closely fits the patient during use, said sheet further having its tail end split longitudinally into a right tail and a left tail by a substantially rectangular-shaped cut-out, said right tail and said left tail each having a distal end and being efficiently long and wide to allow said tails to pass over the iliac crest of the patient such that binder surrounds the abdomen and iliac crest of the patient during use; and said right tail and said left tail have their distal ends means for affixing the distal ends of each of said right and left tails to the cut-out end of said sheet, wherein the binder is held in adjustable compression against the iliac crest and abdomen.

2. The binder as in claim 1 wherein individually sized and fitted cut-outs are provided in said inelastic sheet proximate the anus of the patient and proximate the genitals of the patient during use, said cut-outs allow the binder to be worn during the entire post operative period.

3. A binder as in claim 2 wherein the said tails removeably attach to said sheet by means of Velcro® fasteners.

* * * * *